United States Patent [19]

Sorochenko et al.

[11] Patent Number: 4,746,496
[45] Date of Patent: May 24, 1988

[54] CASE FOR STERILIZATION AND STERILE STORAGE OF OBJECTS

[75] Inventors: Oleg A. Sorochenko; Viktor M. Gutorov, both of Kharkov, U.S.S.R.

[73] Assignee: Kharkovsky Nauchno-Issledovatelsky Institut Obschei I Neotlozhnoi Khirugii, Kharkov, U.S.S.R.

[21] Appl. No.: 773,005

[22] PCT Filed: Dec. 21, 1983

[86] PCT No.: PCT/SU83/00048
§ 371 Date: Dec. 9, 1985
§ 102(e) Date: Dec. 9, 1985

[87] PCT Pub. No.: WO85/02773
PCT Pub. Date: Jul. 4, 1985

[51] Int. Cl.[4] ............................ A61L 2/00; A61L 2/18
[52] U.S. Cl. ................................ 422/292; 422/36; 422/298
[58] Field of Search .................... 422/28, 29, 36, 298, 422/305, 292; 134/31, 40; 206/0.5, 204, 210, 213.1, 438, 439, 561

[56] References Cited

U.S. PATENT DOCUMENTS

| | | | |
|---|---|---|---|
| 3,741,378 | 6/1973 | Parker | 206/210 X |
| 3,881,868 | 5/1975 | Duke | 206/63.5 X |
| 3,884,635 | 5/1975 | Sloan | . |
| 3,904,102 | 9/1975 | Chu et al. | 134/31 X |
| 3,955,922 | 5/1976 | Moulthrop | 312/209 X |
| 4,381,285 | 4/1983 | Wittenberg | . |
| 4,544,529 | 10/1985 | Hoeck | 422/298 X |

Primary Examiner—Barry S. Richman
Assistant Examiner—Lynn Kummert
Attorney, Agent, or Firm—Fleit, Jacobson, Cohn & Price

[57] ABSTRACT

A case for sterilization and sterile storage of objects comprises a hermetic housing (1), a partition (7) with one or several holes (10) dividing the interior of the housing (1) into two sections (8, 9), one of the sections being occupied by a sterilizing liquid, whereas the other accommodating holders (20) for the objects being sterilized. The section (8) for the sterilizing liquid occupies the lower part of the housing. The holes (10) of the partition (7) are grouped in its central portion and each of these holes (10) is provided with a tube (11) facing by its free end the inside of the section (8). The section (8) has on its wall opposite to the partition (7) a spherical projection (12) facing by its convex side the interior of the section (8).

4 Claims, 2 Drawing Sheets

CASE FOR STERILIZATION AND STERILE STORAGE OF OBJECTS

FIELD OF THE INVENTION

This invention relates to medical practice, and more particularly to cases for sterilization and sterile storage of objects.

BACKGROUND OF THE INVENTION

There is known the KM-2 case for sterilization and sterile storage of the "Record" syringe and syringe needles (cf., pamphlet of the "Medexport" Foreign Trade Organization).

This known case comprises a housing with an airtight cover accommodating holders for the syringe and needles. These objects are sterilized by immersion in an alcoholic solution preliminarily admitted to the housing.

The above case requires that the instruments be immersed in a sterilizing solution, which means that surgical instruments are not ready for immediate use, whereas with respect to electrosurgical instruments such method of sterilizing and such a case for sterile storage are absolutely inadequate.

There is also known a case for sterilization and sterile storage of objects comprising an air-tight housing, a cover plate, holders, and a partition with holes to divide the interior of the housing into two sections of which one section contains a sterilizing liquid and the other accommodates the holders (cf., e.g., U.S. Pat. No. 3,881,868, published 1975).

The above case sterilizes by vapours of the sterilizing liquid flowing through the holes in the partition to the section accommodating the holders. The case is advantageous for use when it is stationary, whereas when carrying such a case the sterilizing liquid tends to enter through the holes in the partition to the section accommodating the objects.

SUMMARY OF THE INVENTION

This invention is directed toward the provision of a case for sterilization and sterile storage of objects having means preventing a sterilizing liquid from reaching the objects when the case is handled, such as when carrying the case.

The aims of the invention are attained by that in a case for sterilization and sterile storage of objects comprising an air-tight housing with a cover plate, a partition having one or several holes dividing the interior of the housing into two sections of which one section contains a sterilizing liquid and the other accommodates holders of the objects, according to the invention, the section for the sterilizing liquid is disposed in the bottom portion of the housing, the holes of the partition are grouped in the central part thereof with each of the holes having a coaxial tube the free end of which faces the interior of this section, this section being further provided on the wall opposite to the partition in front of the holes with a spherical projection equal in size to the space occupied by the holes and the convex side of the projection faces the interior of the section for the sterilizing liquid.

Preferably, the tubes taper toward their free ends.

Alternatively, the partition has the form of a truncated cone tapering toward the interior of the section for the sterilizing liquid, the holes being grouped at the smaller base of the cone.

Advisably, the section for storing the objects is provided with another partition arranged in close proximity to the first partition and provided with holes somewhat offset relative to the holes in the firs partition.

Desirably, the case is provided with a gasket of porous moisture-absorbing material arranged on the second partition.

In view of the foregoing, the case for sterilization and sterile storage of objects embodying the present invention prevents penetration of the sterilizing liquid to the section accommodating the sterilized objects, such as electrosurgical instruments. The proposed case is simple to construct and reliable. Also, the case stores electrosurgical instruments which are at any time ready for immediate use to faciliate electrosurgery outdoors.

BRIEF DESCRIPTION OF THE DRAWINGS

The invention will now be described in greater detail with reference to various specific embodiments thereof taken in conjunction with the accompanying drawings, in which.

BEST MODE OF CARRYING OUT THE INVENTION

Figure 1:
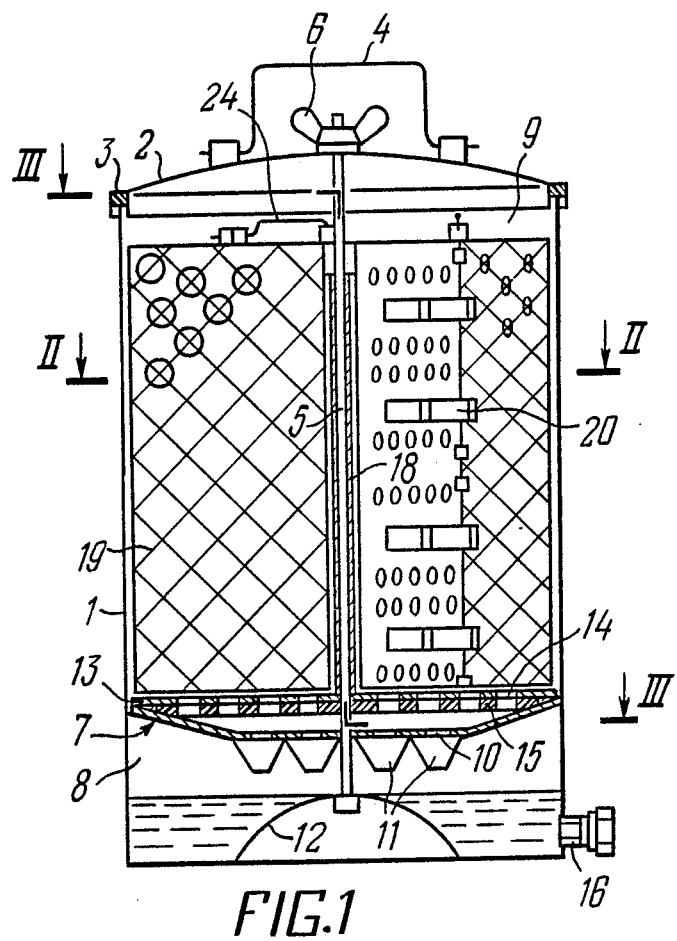
FIG. 1 is a longitudinal sectional view of a case for sterilizing and sterile storage of objects.
Figure 2:
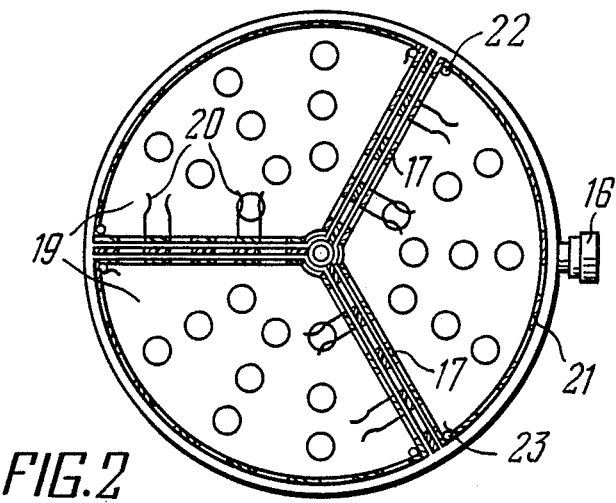
FIG. 2 is a section taken along the line II—II in FIG. 1.
Figure 3:
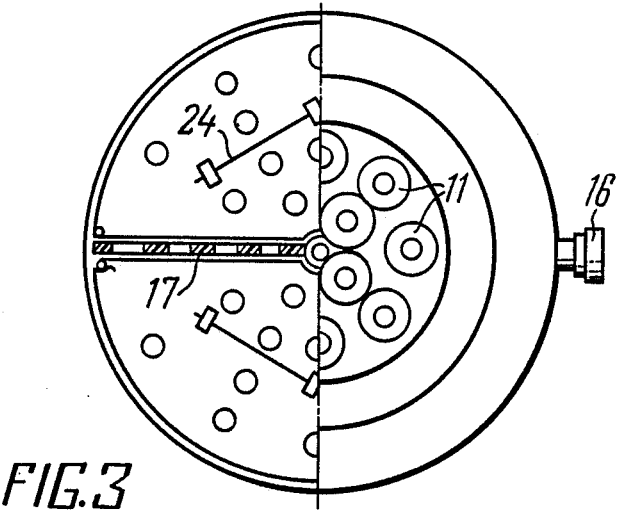
FIG. 3 is a section taken along the line III—III in FIG. 1.

A case for sterilizing and sterile storage of objects, such as surgical instruments, comprises a housing 1 having a cover plate 2 and a sealing gasket 3. The cover plate 2 has a handle 4 for carrying the case and is hermetically secured on the housing 1 by means of a bolt 5 and nut 6.

The lower part of the housing 1 accommodates a partition 7 dividing the interior of the housing 1 into two sections 8 and 9, the lower section 8 containing a liquid antiseptic, whereas the upper section 9 accommodates the instruments. The partition 7 has through holes 10 in its central portion, each such hole 10 being provided with a tube 11 facing the interior of the section 8. The tubes 11 are tapered toward their free ends.

Provided in the section 8 for the liquid antiseptic on the wall opposite to the partition 7 in front of the holes 10 is a spherical projection 12 equal in size to the area occupied by the holes 10 and having its convex side facing the interior of the section 8.

The partition 7 has the form of a truncated cone tapering toward the inside of the section 8, the holes 10 occupying the smaller cone base.

The section 9 for storing instruments is provided with another partition 13 arranged in close proximity to the partition 7 and having holes 14 with hole axes offset relative to the axes of the holes 10. Bonded to the partition 13 is a gasket 15 of comparable configuration fabricated from a porous moisture absorbing material, such as Porolon. The section 8 has a pipe 16 for feeding and discharging the liquid antiseptic. The section 9 for storing instruments is separated by vertical perforated walls 17 into three compartments. The walls 17 are affixed to a central sleeve 18 slipped on the bolt 5. Each compartment of the section 9 has a container 19 with perforated walls, the container being similar in shape to the shape of the compartment. The containers 19 have instrument holders 20. Each container is provided with a pivotable door 21 secured on a hinge 22 and having a locking means 23 to keep it shut. Handles 24 are further provided on the tops of the perforated containers 19.

When using a volatile liquid antiseptic, the partition 7 must have only one centrally arranged hole 10 with a tube 11 (not shown).

The case for sterilization and sterile storage of objects is used in the following manner.

Pre-sterilized instruments are placed into the containers 19, for which purpose these containers 19 are withdrawn from the housing 1 of the case by preliminarily removing the cover plate 2. Thereafter, the containers 19 with the instruments are placed in the housing 1 and the housing 1 is hermetically closed by the cover plate 2 sealed by the gasket 3 by tightening the nut 6 on the bolt 5. To the section 8 liquid antiseptic formalin is fed to fill the space between the side walls of section 8 and sphere 12, after which the pipe 16 is closed.

Formalin vapours escape from the section 8 through the tubes 11, holes 10 in the partition 7 and, having passed through the holes in the Porolon gasket 15 and holes 14 of the partition 13, these vapours enter through the perforations the interior of the containers 19 to occupy the space of the section 9. The instruments in the containers 19 are therefore continuously subjected to the action of formula vapours, which ensures that they are always ready for immediate use.

To make use of the instruments, the cover plate 2 is removed and the containers 19 are retrieved from the housing 1 by the handles 24; access to the instruments being assured by opening the doors 21.

The arrangement of the section 8 in the form of a hollow cylinder having the top portion thereof provided with the tapering downwards through tubes 11 prevents the escape of the liquid antiseptic to the space above the section 8 in any position of the case, including the upside down position, which ensures reliable protection of the instruments in the compartments from the liquid antiseptic. The provision of the spherical projection 12 makes the space under the inlets of the tubes 11 free of the liquid antiseptic, which prevents partial penetration of the liquid antiseptic to these tubes 11 when the case is suddenly overturned. The tapered surface of the partition 7 provides space for the liquid antiseptic when the case tumbles or even turns over.

Spatters of the liquid antiseptic fail to reach the instruments during vibrations or jerks of the case thanks to the Porolon gasket 15, because such spatters entering through the tubes 11 are absorbed and partially reflected by the surface of the partition 15.

Apart from formalin, used as the liquid antiseptic can be any volatile liquid substances to ensure the required degree of sterilization for each particular application.

INDUSTRIAL APPLICABILITY

A case for sterilization and sterile storage of objects according to the invention can find application in the medical practice and veterinary medicine for storing surgical instruments, catheters, tubes, heart valves and either prostheses which are not subject to boiling sterilization. The proposed case is preferably intended for sterilization and storing of electrosurgical instruments, especially when delivering them to operation wards or in the outdoor conditions.

We claim:

1. A case for sterilization and sterile storage of objects comprising: a hermetic housing with a cover plate, a first partition having one or more holes dividing the interior of the housing into two sections, a first section for containing a volatile sterilizing liquid, and a second section for storing objects and for accommodating instrument holders, wherein the first section for the volatile sterilizing liquid is disposed in the bottom portion of the housing, and wherein the holes of the first partition are grouped in the central part thereof with each of the holes having a coaxial tube having a free end facing the interior of the first section, each said tube tapering inwardly toward its free end, the first section including a spherical projection on a wall opposite to the partition and in front of the holes, the spherical projection being equal in size to the area occupied by the holes and having its convex side facing the interior of the first section for the sterilizing liquid.

2. A case as claimed in claim 1, wherein the partition has the form of a truncated cone tapering inwardly toward the interior of the first section for the sterilizing liquid and defining a smaller base, the holes in the first partition being grouped on the smaller base of the truncated cone.

3. A case as claimed in claim 1, wherein the second section for storing the objects includes a second partition arranged in close proximity to the first partition and having holes offset relative to the holes in the first partition.

4. A case as claimed in claim 3, wherein a gasket of porous, moisture-absorbing material is disposed on the second partition.

* * * * *